US010323198B1

(12) United States Patent
Harvey

(10) Patent No.: US 10,323,198 B1
(45) Date of Patent: *Jun. 18, 2019

(54) HIGH DENSITY RENEWABLE FUELS FROM ZIZAENES

(71) Applicant: The United States of America, as Represented by the Secretary of the Navy, Washington, DC (US)

(72) Inventor: Benjamin G Harvey, Ridgecrest, CA (US)

(73) Assignee: The United States of America as Represented by the Secretary of the Navy, Washington, DC (US)

(*) Notice: Subject to any disclaimer, the term of this patent is extended or adjusted under 35 U.S.C. 154(b) by 255 days.

This patent is subject to a terminal disclaimer.

(21) Appl. No.: 14/919,529

(22) Filed: Oct. 21, 2015

Related U.S. Application Data

(63) Continuation-in-part of application No. 14/314,305, filed on Jun. 25, 2014, now Pat. No. 9,493,717, and
(Continued)

(51) Int. Cl.
C10L 1/04 (2006.01)
C07C 5/31 (2006.01)
C07C 5/03 (2006.01)
C10L 1/08 (2006.01)
C10L 1/18 (2006.01)
C10L 10/12 (2006.01)
(Continued)

(52) U.S. Cl.
CPC ........ C10L 1/04 (2013.01); C07C 5/03 (2013.01); C07C 5/31 (2013.01); C10L 1/08 (2013.01); C10L 1/18 (2013.01); C10L 10/12 (2013.01); C10M 101/02 (2013.01); C07C 2523/42 (2013.01); C07C 2531/06 (2013.01); C10L 1/1832 (2013.01); C10L 2200/0469 (2013.01);
(Continued)

(58) Field of Classification Search
CPC .................................. C10L 1/14; Y02E 50/10
See application file for complete search history.

(56) References Cited

U.S. PATENT DOCUMENTS 7,846,222 B2  12/2010  Renninger et al.
8,703,454 B2   4/2014  Schalk et al.
(Continued)

FOREIGN PATENT DOCUMENTS

WO   WO 2010134004 A1 * 11/2010 ............... C12N 9/88

OTHER PUBLICATIONS

Peralta-Yahya, P. P. et al. Identification and microbial production of a terpene-based advanced biofuel. Nat. Commun. 2:483 doi: 10.1038/ncomms1494 (2011).*
(Continued)

Primary Examiner — Ellen M McAvoy
Assistant Examiner — Ming Cheung Po
(74) Attorney, Agent, or Firm — Charlene A. Haley

(57) ABSTRACT

A process for making high density fuels having the potential to increase the range and/or loiter time of Navy platforms. Derivation of these fuels from a sustainable source will decrease the carbon footprint of the Department of Defense (DoD) and reduce reliance on nonsustainable petroleum sources. Fuels based on ziza-anes have volumetric net heats of combustion up to ca. 18% higher than conventional Navy jet fuel (JP-5). Moreover, ziza-anes can be generated from sustainable biomass sugars via fermentation.

14 Claims, 3 Drawing Sheets

Related U.S. Application Data a continuation-in-part of application No. 13/676,541, filed on Nov. 14, 2012, now Pat. No. 9,994,498.

(60) Provisional application No. 61/840,322, filed on Jun. 27, 2013, provisional application No. 61/562,681, filed on Nov. 22, 2011.

(51) Int. Cl.
*C10M 101/02* (2006.01)
*C10L 1/183* (2006.01)

(52) U.S. Cl.
CPC ... *C10L 2230/081* (2013.01); *C10L 2270/026* (2013.01); *C10L 2270/04* (2013.01); *C10L 2290/24* (2013.01)

(56) References Cited

U.S. PATENT DOCUMENTS

| | | | | |
|---|---|---|---|---|
| 9,963,652 | B1* | 5/2018 | Harvey | C07C 5/03 |
| 9,994,498 | B2* | 6/2018 | Harvey | C10L 1/04 |
| 2008/0092829 | A1 | 4/2008 | Renninger et al. | |
| 2009/0020089 | A1 | 1/2009 | Ryder et al. | |
| 2009/0020090 | A1 | 1/2009 | Ryder et al. | |
| 2009/0272119 | A1 | 11/2009 | Ryder | |
| 2009/0272352 | A1 | 11/2009 | Ryder | |
| 2011/0056869 | A1* | 3/2011 | Novak | C10G 45/58 208/49 |
| 2012/0116138 | A1* | 5/2012 | Goodall | C10G 45/08 585/357 |
| 2013/0298861 | A1 | 11/2013 | Lee et al. | |

OTHER PUBLICATIONS

Consequences of Conformational Preorganization in Sesquiterpene Biosynthesis: Young J. Hong and Dean J. Tantillo Journal of the American Chemical Society 2009 131 (23), 7999-8015DOI: 10.1021/ja9005332.*
Koji NAkanishi, Toshio Goto, Sho Ito, Natural Products Chemistry, vol. 1 pp. 134 Oct. 2013.*
U.S. Appl. No. 13/676,541, Benjamin Harvey.
U.S. Appl. No. 13/604,115, Benjamin Harvey.

* cited by examiner

HIGH DENSITY RENEWABLE FUELS FROM ZIZAENES

CROSS-REFERENCE TO RELATED APPLICATIONS

This is a continuation-in-part patent application of, claiming the benefit of, parent application Ser. No. 13/676,541 filed on Nov. 14, 2012, which claims benefit of patent application Ser. No. 61/562,681 filed on Nov. 22, 2011, and is a continuation-in-part patent application of, claiming benefit of patent application Ser. No. 14/314,305 filed on Jun. 25, 2014, which claims benefit of patent application Ser. No. 61/840,322 filed on Jun. 27, 2013, whereby the entire disclosures of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor. The Government and Contractor has certain rights in inventions made by the contractor and the Government employees while performing under the work statement of a Government funding agreement in Cooperative Research and Development Agreement (CRADA) #NCRADA-NAWCWDCL-14-255.

FIELD OF THE INVENTION

The invention generally relates to the conversion of sesquiterpenes to high density fuels. High density fuels have the potential to increase the range and/or loiter time of Navy platforms. Derivation of these fuels from a sustainable source will decrease the carbon footprint of the Department of Defense (DoD) and reduce reliance on nonsustainable petroleum sources.

Figure 1:
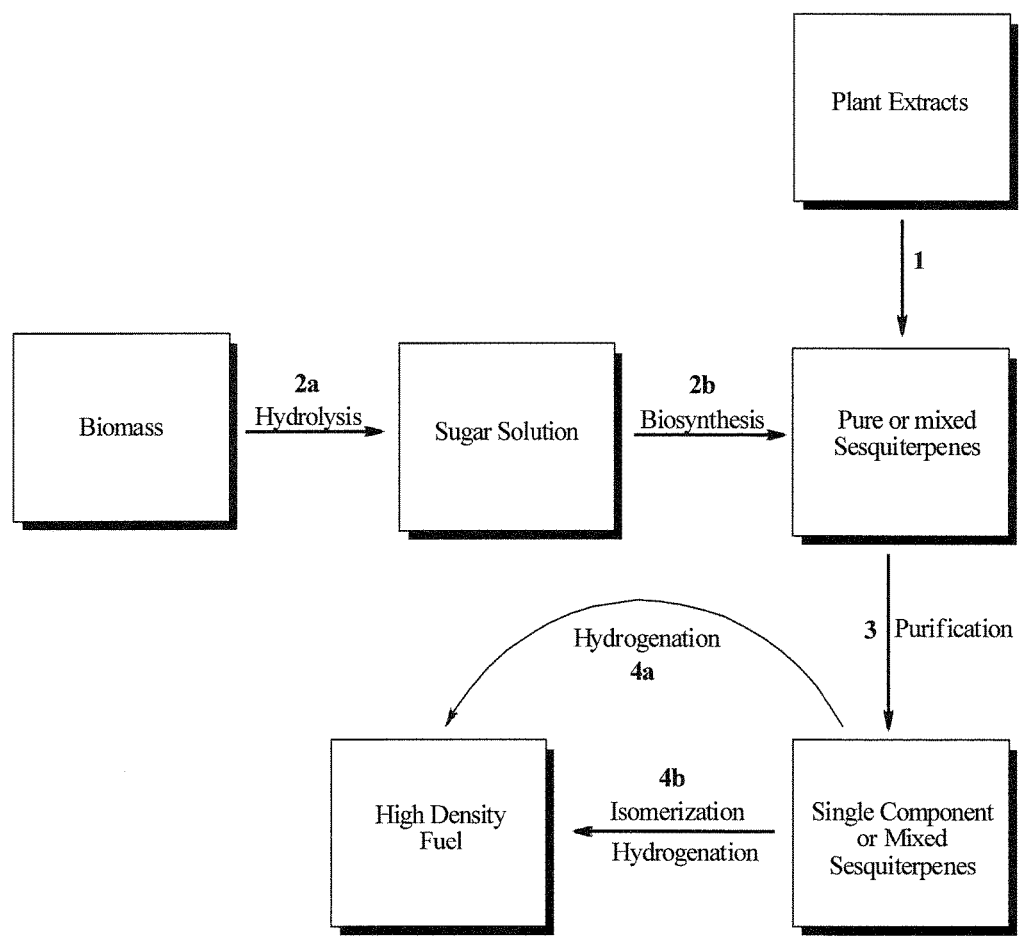
FIG. 1 is a block diagram illustrating the steps to produce high density biofuels from sesquiterpenes, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

The invention generally relates to the conversion of sesquiterpenes to high density fuels. High density fuels have the potential to increase the range and/or loiter time of Navy platforms. Derivation of these fuels from a sustainable source will decrease the carbon footprint of the Department of Defense (DoD) and reduce reliance on nonsustainable petroleum sources.

The range of aircraft and weapon systems is largely dependent on the fuel used for propulsion. Fuels based on ziza-anes have volumetric net heats of combustion up to ca. 18% higher than conventional Navy jet fuel (JP-5). Moreover, ziza-anes can be generated from sustainable biomass sugars via fermentation. Use of these fuels will reduce net carbon emissions while improving the range and loiter time of a variety of Navy platforms.

1. zizaene or isozizaene mixtures are generated via a fermentation process from biomass sugars or natural gas. Alternatively these sesquiterpene mixtures can be isolated from a renewable source, or generated by a metabolically engineered plant.

2. The sesquiterpene blend is purified by fractional distillation or used as a mixture of sesquiterpenes.

3. Alternatively, the mixture can be dimerized to yield a mixture rich in C30 hydrocarbons.

4. The product mixture is hydrogenated to generate ziza-ane mixtures.

5. Saturated mixtures are suitable as standalone fuels or blended with other fuels to achieve desired properties. Additives, including cetane enhancers can be added to the reduced sesquiterpenes to generate full-performance jet or diesel fuels. Dimerized mixtures have utility as lubricants.

The following are descriptions of some embodiments of the invention.

1. A mixture of zizaene, prezizaene, and other sesquiterpenes is generated from substrates including biomass sugars or natural gas via a fermentation process. In embodiments, a mixture including isozizaene is generated. Feedstocks can include cellulose, hemicellulose, and lignocellulosic materials. Alternatively, mixtures of sesquiterpenes including zizaene or isozizaene can be isolated from plant extracts by steam distillation.

2. In embodiments, a mixture comprising >75% zizaene along with additional sesquiterpenes is isolated. In other embodiments, a zizaene or isozizaene enriched mixture is isolated by fractional distillation.

3. In embodiments, the sesquiterpene mixture is dimerized to generate a lubricant mixture. The mixture can be dimerized thermally or in the presence of a homogenous or heterogeneous catalyst. In embodiments the catalyst is an acid catalyst including zeolites, aluminosilicates, clays, cation exchange resins, etc.

4. Antioxidants including phenolics are added to the unsaturated sesquiterpene mixture to increase the storage stability of the hydrocarbons. In a preferred embodiment, the sesquiterpene mixture is hydrogenated in the presence of a catalyst under a hydrogen atmosphere to obtain a saturated sesquiterpene mixture. In embodiments the hydrogenation is conducted in acetic acid. In embodiments, the unsaturated fuel has a density of 0.94 g/mL, a volumetric net heat of combustion (NHOC) of 147.4 kBtu/gal, a flashpoint of 98° C., a −20° C. dynamic viscosity of 28.2 cP, a 40° C. dynamic viscosity of 3.93 cP, and a glass transition temperature of −94° C. In embodiments, the saturated sesquiterpene mixture has a density of 0.929 g/mL, a volumetric net heat of combustion of 141.9 kBtu/gal, a −20° C. dynamic viscosity of 42.9 cP, a 40° C. dynamic viscosity of 4.3 cP, and a glass transition temperature of −94° C. In other embodiments, either the unsaturated or saturated sesquiterpene mixture is isomerized with an acid catalyst for the purposes of decreasing the viscosity, increasing the density and net heat of combustion, or increasing the cetane number. In embodiments, the product of the isomerization reaction includes a diamondoid structure. In embodiments the isomerized mixture is purified by fractional distillation.

5. Fuel mixtures including unsaturated sesquiterpene blends and saturated sesquiterpene blends are combined with other renewable or petroleum-based fuels. In embodiments the sesquiterpene fuels are blended with Jet-A, JP-8, JP-5, JP-10, RJ-4, F-76, commercial diesel fuel. In other embodiments, the sesquiterpene/pane fuels are blended with high cetane fuels derived via a Fischer-Tropsch process or Alcohol-to-Jet (ATJ) process to generate fuels with cetane numbers in the range of 30-50. In other embodiments the sesquiterpene/pane fuels are blended with nitrate esters or other cetane enhancers in low concentration to yield fuels with increased cetane numbers.

Embodiments of the invention generally relate to methods for manufacturing turbine and diesel fuels including, providing a sesquiterpene mixture having zizaene(s), and generated by metabolically engineered organisms from substrates including glucose, sucrose, fructose, other reducing sugars, cellobiose, cellulose, hemicellulose, lignocellulose, lignin, methane and $CO_2$, or isolated from plant material by solvent extraction or steam distillation, purifying the sesquiterpene mixture to produce pure zizaene or pure sesquiterpene mixtures, isomerizing the pure zizaene or pure sesquiterpene mixtures with at least one heterogeneous or homogenous acid catalyst to produce isomers, hydrogenating the isomers with at least one hydrogenation catalyst under hydrogen pressure, and distilling said isomers to produce a first high density fuel and a higher molecular weight residue, or further isomerizing the isomers with at least one Lewis acid catalyst to generate a hydrocarbon mixture having adamantanes and distilling the adamantane mixture to produce a second high density fuel mixture and a higher molecular weight residue.

In embodiments, the sesquiterpene mixture has >75 weight % zizaene. In embodiments the sesquiterpene mixture has zizaene, prezizaene, isozizaene in any proportional combination thereof. In embodiments, the residue obtained after distillation of the first or the second high density fuel is purified by vacuum distillation to yield a lubricant composed primarily of C30 hydrocarbons. In embodiments, the hydrogenation catalyst has at least one metal selected from the group consisting of Ni, Cu, Pd, Pt, and Ru. In embodiments, the heterogeneous or homogenous acid catalyst is selected from the group consisting of at least one of perfluorinated sulfonic acid resins, cross-linked sulfonic acid resins, acid clays, zeolites, polyphosphoric acid, cation exchange resins, Lewis acid catalysts, supported Brønsted acid catalysts, metal oxides, mineral acids including $H_2SO_4$ and $H_3PO_4$, and any mixtures thereof. In embodiments, the Lewis acid catalyst is selected from $AlCl_3$, $AlBr_3$, $AlI_3$, Lewis acidic ionic liquids, $BF_3$, gallium triflate, indium triflate, and other strong Lewis acids, and any combination thereof.

In embodiments, the first or second high density fuel has a density >0.92 g/mL and a volumetric net heat of combustion >140,000 btu/gal. In embodiments, the first high density fuel or the second high density fuel mixture is blended with cetane enhancers including alkyl nitrates to generate fuels with cetane numbers >40. In embodiments, the first high density fuel or the second high density fuel mixture has a dynamic viscosity between about 25 and 50 cP at −20° C. In embodiments, the first high density fuel or the second high density fuel mixture has a dynamic viscosity <5 cP at 40° C. In embodiments, the first high density fuel or the second high density fuel mixture is blended with petroleum-based fuels including JP-10, RJ-4, JP-8, JP-5, F-76, Diesel #2, and Jet A. In embodiments, the first high density fuel or the second high density fuel mixture is blended with a high cetane blendstock including fuels generated via a Fischer-Tropsch process, ethylene oligomerization, butene oligomerization, or hexene oligomerization, to generate fuels with cetane numbers >40. In embodiments, the lubricant has a dynamic viscosity >20 cP at 40° C. In embodiments, the purified sesquiterpenes are combined with antioxidants including BHT, renewable phenols, and used as fuels without hydrogenation.

Another aspect of the invention generally relates to fuels produced by the methods herein. Another aspect of the invention generally relates to methods for manufacturing turbine and diesel fuels including, providing a sesquiterpene mixture having zizaene, and generated by metabolically engineered organisms from substrates including glucose, sucrose, fructose, other reducing sugars, cellobiose, cellulose, hemicellulose, lignocellulose, lignin, methane and $CO_2$, or isolated from plant material by solvent extraction or steam distillation, and purifying the sesquiterpene mixture to produce pure zizaene or sesquiterpene mixtures, hydrogenating the pure zizaene or pure sesquiterpene mixture with at least one hydrogenation catalyst under hydrogen pressure, and distilling the isomers to produce a high density fuel.

Figure 2:
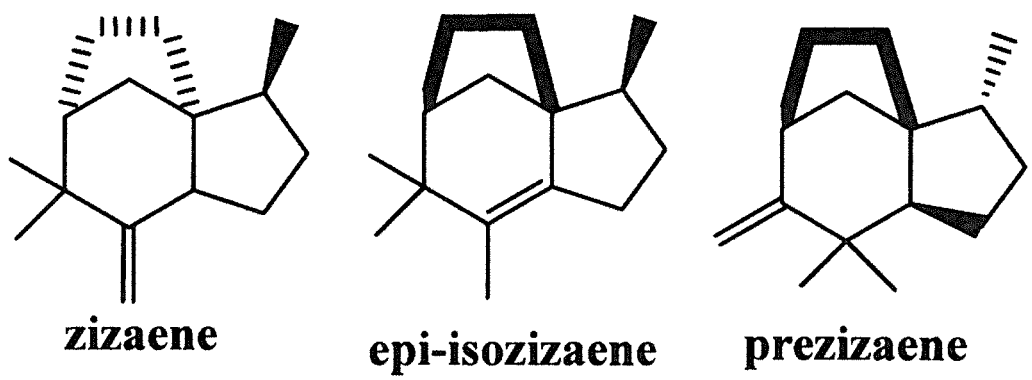
FIG. 2 is a flow diagram illustrating sesquiterpene structures, according to embodiments of the invention.

FIG. 2 is a flow diagram illustrating sesquiterpene structures, according to embodiments of the invention.

Figure 3:
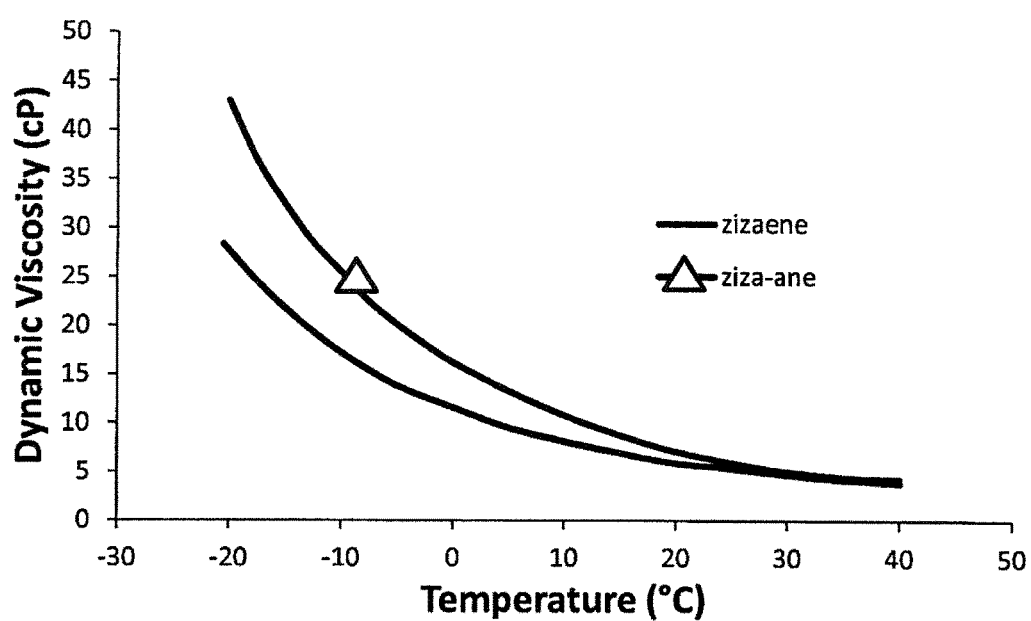
FIG. 3 is a graph illustrating the dynamic viscosity data for zizaene and ziza-ane fuel mixtures, according to embodiments of the invention.

FIG. 3 is a graph illustrating the dynamic viscosity data for zizaene and ziza-ane fuel mixtures, according to embodiments of the invention.

The biosynthesis of farnesene and use as a standalone diesel/jet fuel or component of same is covered in the following USPTO applications: 20090272352, 20090272119, 20090020090, 20090020089, and 20080092829. Farnesane, the reduced form of farnesene, is a linear sesquiterpene of relatively low density (0.766 g/mL). U.S. Pat. No. 7,846,222 describes farnesene-based jet and diesel fuels. US patent application 20130298861 describes biosynthetic methods to generate bisabolene and discusses some fuels derived from bisabolene.

High density fuels have applications in a variety of Navy platforms including jet aircraft, ships, missiles, and UAVs. The fuels developed herein will help to meet Navy goals focused on the use of renewable and sustainable fuels while providing improved performance over conventional, petroleum-based fuels.

Embodiments of this invention describe the conversion of sesquiterpenes to high density fuels. The sesquiterpenes can be either extracted from plants or specifically produced by bioengineered organisms from waste biomass. This approach allows for the synthesis of high performance renewable fuels.

Embodiments of the invention detail processes for conversion of sesquiterpenes to high density fuel mixtures. Aspects of the process include hydrogenation of the sesquiterpenes to improve stability of the fuels as well as selective isomerization of the sesquiterpenes to improve density, net heat of combustion, low temperature viscosity, and cetane number. The isomerization process can be carried out with heterogeneous catalysts at moderate temperatures and requires no solvent. Thus, embodiments of the invention provide a route for the sustainable production of renewable, ultra-performance fuels.

The general procedure for synthesizing high density sesquiterpene fuels is as follows:

1. A pure sesquiterpene or mixture of sesquiterpenes are either extracted from plant sources (e.g. clove oil) or 2. a) A biomass source (including lignocellulosic, cellulosic, or hemicellulosic feedstocks) is hydrolyzed to produce a sugar solution b) The sugar solution is fermented to a sesquiterpene or mixture of sesquiterpenes by a bioengineered organism.

3. The hydrocarbons are purified by solvent extraction, pervaporation, membrane separation, or distillation.

4. Pure sesquiterpenes or mixtures are then:

a) Directly hydrogenated and distilled to yield a liquid fuel or b) Isomerized with heterogeneous acidic catalysts to produce a pure compound or complex mixture of hydrocarbons which is then hydrogenated and distilled to yield a liquid fuel.

Process:

1. A pure sesquiterpene or mixture of sesquiterpenes is isolated from a plant source. This can be accomplished by steam distillation, solvent extraction, or pyrolysis, among other techniques.

2a. In an alternate approach, biomass can be hydrolyzed to produce a sugar solution. This step can be accomplished by physical, chemical, or enzymatic methods, or any combination thereof.

2b. The sugar solution is used as a food source for bioengineered organisms that produce sesquiterpenes in either a batch or continuous mode.

3. Regardless of the source, the sesquiterpenes can be upgraded through techniques including fractional distillation, chemical treatments, and extractions to produce a suitably pure hydrocarbon feedstock composed of either a single sesquiterpene or complex mixture of sesquiterpenes. In the case of the biosynthesized sesquiterpenes (2b), the major impurity is water which can be effectively removed by both membrane separation techniques as well as by distillation.

4a) Sesquiterpenes are directly hydrogenated to produce a high density fuel. Catalysts based on Ni, Pd, Pt, Cu, and Ru can be utilized under moderate hydrogen pressures.

4b) To improve specific fuel properties such as viscosity, net heat of combustion, density, and cetane number, sesquiterpenes can be readily isomerized with heterogeneous acid catalysts including, but not limited to; Nafion, Amberlyst. Montmorillonite K-10, zeolites and supported polyphosphoric acid. Sesquiterpenes can also be effectively isomerized with Lewis acids and mineral acids. After isomerization, these sesquiterpenes can be hydrogenated as in 4a. Pure sesquiterpenes or defined mixtures of sesquiterpenes can be isolated by fractional distillation to generate fuels with specific properties. FIG. 1 is a block diagram overview showing the steps of the embodiments of the invention therein.

Example 1 (high catalyst loading). 50 mL of caryophyllene (technical grade) is combined with 500 mg of Nafion SAC-13 in a flask. The mixture is vigorously stirred and heated to 100° C. overnight. The pale yellow solution is decanted, hydrogenated at 50 psig $H_2$ with 50 mg $PtO_2$ as catalyst. The resulting mixture is filtered and vacuum distilled to yield a colorless fuel mixture including saturated hydrocarbons derived from seven main isomers including α-neoclovene, clovene, and α-panasinsene (see Schematic 1).

Schematic 1. Products resulting from the acid-catalyzed isomerization of β-caryophyllene. Numbers under the structures represent the weight percentage of each molecule. The first number results from low catalyst loading, while the number in parentheses results from high catalyst loading as described in the process.

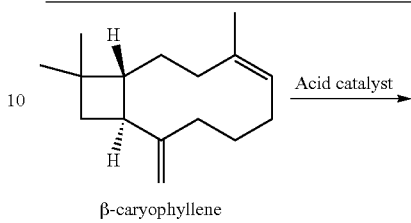

β-caryophyllene

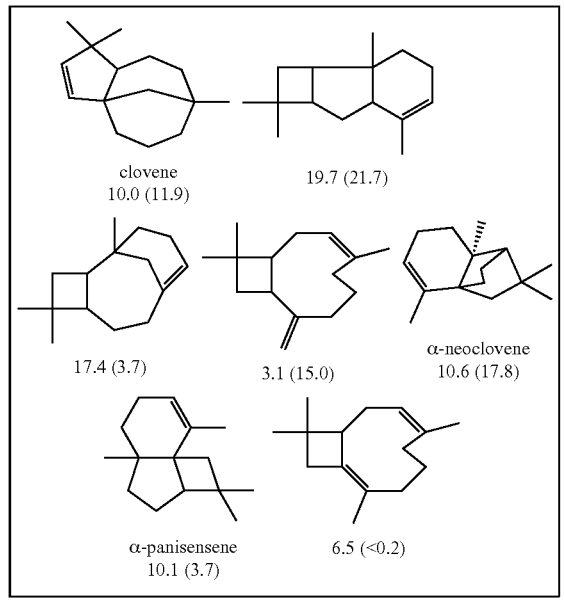

clovene
10.0 (11.9)

19.7 (21.7)

17.4 (3.7)

3.1 (15.0)

α-neoclovene
10.6 (17.8)

α-panisensene
10.1 (3.7)

6.5 (<0.2)

Example 2 (low catalyst loading). 500 mL of caryophyllene is combined with 2 g of Nafion SAC-13 in a flask and subjected to the same conditions as in Example 1. A significantly different product distribution results (see Schematic 1).

Example 3. 175 mL of valencene (Scheme 3) biosynthesized from sucrose is hydrogenated at 50 psig $H_2$ with 100 mg $PtO_2$ as catalyst. After hydrogenation the catalyst flocculates and the catalyst is separated by decantation. The properties of this fuel mixture are listed in Table 1.

Example 4. 175 mL of premnaspirodiene (Scheme 3) biosynthesized from sucrose is hydrogenated as in Example 3. The properties are listed in Table 1.

Example 5. 175 mL of commercial caryophyllene (technical grade) is hydrogenated as in Example 3. The properties are listed in Table 1.

Example 6. 5 g of valencene biosynthesized from sucrose are combined with 0.1 g of Nafion SAC-13 and the mixture is stirred and heated to 100° C. for 16 h. The solution is decanted to yield a mixture of isomers.

Example 7. 5 g of premnaspirodiene biosynthesized from sucrose is isomerized as described in Example 6.

TABLE 1

Key Properties of Sesquiterpene Fuels.
Table 1. Key Properties of Sesquiterpene Fuels

| Sesquiterpene | Density (g/mL) | NHOC (btu/gal) | 40° C. Viscosity (cSt) | −20° C. Viscosity (cSt) | Ignition Delay (ms) | Derived Cetane No. |
|---|---|---|---|---|---|---|
| Valencane | 0.879 | 135,386 | 4.417 | 50.24 | 10.562 | 23.26 |
| Caryophyllane | 0.85 | 132,790 | 4.067 | 60.47 | 9.75 | 24.52 |
| Prenmaspirodiane | 0.882 | 135,564 | 3.812 | 42.91 | 7.779 | 28.65 |
| HDCL-8 | 0.90 | 137,800 | 53.58 | NM | 13.173 | 20.23 |
| HDCL-9 | 0.90 | 137,100 | 5.07 | 61.96 | 6.549 | 32.53 |
| HDCL-10 | 0.92 | 140,900 | NM | NM | NM | NM |

Note:
HDCL-8 is the fuel generated from caryophyllene with high catalyst loading. HDCL-9 is the fuel generated with low catalyst loading. The density and net heat of combustion of HDCL-10 has been calculated based on a distillate cut including primarily high-density components (i.e. clovene/neoclovene and assuming a density of 0.92 g/mL).

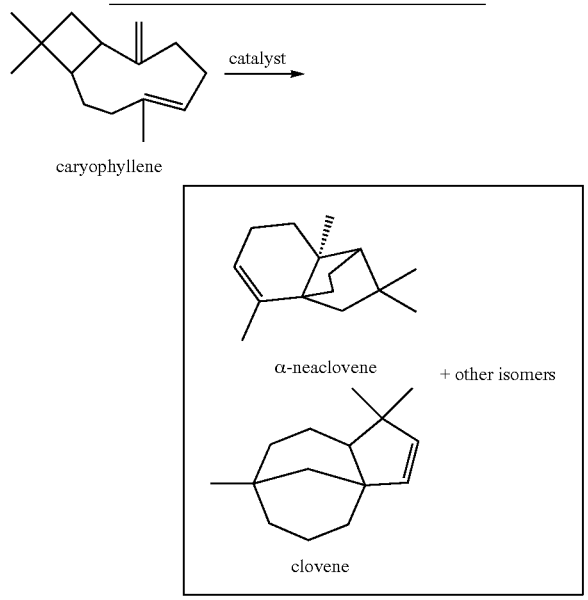

Scheme 2. Isomerization of caryophyllene with a heterogenous acid catalyst.

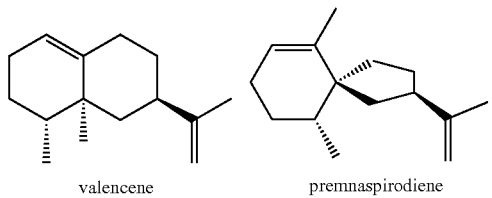

Scheme 3. Structures of valencene and premnaspirodiene.

Embodiments of the invention generally relate to methods for manufacturing jet and diesel fuels including, providing pure and/or mixed sesquiterpenes isolated from plant extracts and/or biosynthesized from biomass, purifying the pure and/or mixed sesquiterpenes to produce single components or mixtures of sesquiterpenes, converting the single component or mixed sesquiterpenes by either, directly hydrogenating the single component or mixed sesquiterpenes with at least one hydrogenation catalyst under hydrogen pressure, or isomerizing either with or without a solvent, the single component or mixed sesquiterpenes with at least one heterogeneous acid catalyst to produce isomers and hydrogenating the isomers with at least one hydrogenation catalyst under hydrogen pressure, and distilling either the hydrogenated single component or mixed sesquiterpenes or the hydrogenated isomers to produce high density fuels.

Another aspect of the invention generally relates to the production and blends of fuels. In embodiments, the pure and/or mixed sesquiterpenes are selected from the group consisting of valencene, premnaspirodiene, caryophyllene, humulene, clovene, neoclovene, panasinsene, thujopsene, longifolene, cubebene, zizaene, santalene, longipinene, isomers of the above sesquiterpenes, other cyclic terpenes, and any mixtures thereof. In embodiments, the single component or mixed sesquiterpenes are selected from the group consisting of caryophyllene, valencene, premnaspirodiene, or any mixture thereof. In embodiments, the isomers are at least one isomer selected from the group consisting of α-neoclovene, clovene, or any mixture thereof. In embodiments, the hydrogenating catalyst having at least one metal selected from the group consisting of Ni, Cu, Pd, Pt, $PtO_2$, Ru and the reaction is conducted without a solvent.

In embodiments, the heterogeneous acid catalyst are selected from the group consisting of at least one of Nafion (perfluorinated sulfonic acid resins), Amberlyst (crosslinked sulfonic acid resins), Montmorillonite K-10, zeolites, polyphosphoric acids, cation exchange resins. Lewis acid catalysts, supported Bronsted acid catalysts, mineral acids including $H_2SO_4$ and $H_3PO_4$, and any mixtures thereof. In embodiments, the plant extracts are selected from the group consisting of clove oil or any essential oil having significant quantities of cyclic sesquiterpenes, and mixtures of said oils. In embodiments, the biomass includes at least one of sucrose, glucose, fructose, cellobiose, other reducing sugars, cellulose, and hemicelluloses in any proportion.

Another aspect of the invention generally relate to methods for manufacturing jet and diesel fuels including, providing pure and/or mixed sesquiterpenes isolated from plant extracts and/or biosynthesized from biomass, purifying the pure and/or mixed sesquiterpenes to produce single components or mixtures of sesquiterpenes producing a first set of fuels, or converting the single component or mixed sesquiterpenes by isomerizing either with or without a solvent, the single component or mixed sesquiterpenes with at least one heterogeneous acid catalyst to produce isomers, and distilling the isomers producing a second set of fuels. All blends of fuels are incorporated into all aspects of the invention.

Yet other aspects of the invention generally relate to a first set of fuels produced from the methods above. Still yet other aspects of the invention generally relate to a second set of fuels produced from the methods above.

In embodiments, the fuels are pure sesquiterpanes or prepared by selective fractional distillation of sesquiterpane mixtures (density >0.90 g/mL, NHOC>137,000 btu/gal). In other embodiments, the fuels are pure sesquiterpanes or generated by selective fractional distillation of sesquiterpane mixtures (cetane number >30). In yet other embodiments, the fuels are generated by blending sesquiterpane mixtures with known cetane enhancers or antioxidants for fuels. In embodiments, the fuels generated by blending sesquiterpene fuels with petroleum-based fuels including JP-10, RJ-4, JP-8, JP-5, F-76, Diesel #2, Jet A, and any renewable fuel.

In embodiments, the high density missile/turbine fuels are blends of cyclic sesquiterpanes with JP-10 in a desired proportion. In embodiments, the high density jet fuels are blends of cyclic sesquiterpanes with jet fuels including JP-5, JP-8, and Jet A. In embodiments, the high density diesel fuels are blends of cyclic sesquiterpanes with petroleum-derived diesel fuel. In embodiments, the high density jet/diesel fuels are blends of cyclic sesquiterpanes with fuels generated by ethylene oligomerization. In embodiments, the high density jet/diesel fuels are blends of cyclic sesquiterpanes with fuels generated by butene oligomerization. In embodiments, the high density jet/diesel fuels are blends of cyclic sesquiterpanes with fuels generated by hexene oligomerization. In embodiments, the high density jet/diesel fuels are blends of cyclic sesquiterpanes with diesel fuels produced from natural gas.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for manufacturing turbine and diesel fuels, comprising:
   providing a sesquiterpene mixture having zizaene(s), and generated by metabolically engineered organisms from substrates including glucose, sucrose, fructose, other reducing sugars, cellobiose, cellulose, hemicellulose, lignocellulose, lignin, methane and $CO_2$, or isolated from plant material by solvent extraction or steam distillation;
   purifying said sesquiterpene mixture to produce pure zizaene or pure sesquiterpene mixtures;
   isomerizing said pure zizaene or pure sesquiterpene mixtures with at least one heterogeneous or homogenous acid catalyst to produce isomers; and
   hydrogenating said isomers with at least one hydrogenation catalyst under hydrogen pressure to generate hydrogenated isomers; and distilling said hydrogenated isomers to produce a first high density fuel and a higher molecular weight residue; or
   further isomerizing said hydrogenated isomers with at least one Lewis acid catalyst to generate a hydrocarbon mixture having adamantanes and distilling the adamantane mixture to produce a second high density fuel mixture and a higher molecular weight residue.

2. The method according to claim 1, wherein said sesquiterpene mixture having >75 weight % zizaene.

3. The method according to claim 1, wherein said sesquiterpenes mixture having zizaene, prezizaene, isozizaene in any proportional combination thereof.

4. The method according to claim 1 wherein said residue obtained after distillation of said first or said second high density fuel is purified by vacuum distillation to yield a lubricant composed primarily of C30 hydrocarbons.

5. The method according to claim 1 wherein said hydrogenating catalyst has at least one metal selected from the group consisting of Ni, Cu, Pd, Pt, and Ru.

6. The method according to claim 1, wherein said heterogeneous or homogenous acid catalyst is selected from the group consisting of at least one of perfluorinated sulfonic acid resins, cross-linked sulfonic acid resins, acid clays, zeolites, polyphosphoric acid, cation exchange resins, Lewis acid catalysts, supported Brønsted acid catalysts, metal oxides, mineral acids including $H_2SO_4$ and $H_3PO_4$, and any mixtures thereof.

7. The method according to claim 1, wherein said Lewis acid catalyst is selected from $AlCl_3$, $AlBr_3$, $AlI_3$, Lewis acidic ionic liquids, $BF_3$, gallium triflate, indium triflate, and other strong Lewis acids, and any combination thereof.

8. The method according to claim 1, wherein said first or said second high density fuel has a density >0.92 g/mL and a volumetric net heat of combustion >140,000 btu/gal.

9. The method according to claim 1, wherein said first high density fuel or said second high density fuel mixture is blended with cetane enhancers including alkyl nitrates to generate fuels with cetane numbers >40.

10. The method according to claim 1, wherein said first high density fuel or said second high density fuel mixture has a dynamic viscosity between about 25 and 50 cP at −20° C.

11. The method according to claim 1, wherein said first high density fuel or said second high density fuel mixture has a dynamic viscosity <5 cP at 40° C.

12. The method according to claim 1, wherein said first high density fuel or said second high density fuel mixture is blended with petroleum-based fuels including JP-10, RJ-4, JP-8, JP-5, F-76, Diesel #2, and Jet A.

13. The method according to claim 1, wherein said first high density fuel or said second high density fuel mixture is blended with a high cetane blendstock including fuels generated via a Fischer-Tropsch process, ethylene oligomerization, butene oligomerization, or hexene oligomerization, to generate fuels with cetane numbers >40.

14. The method according to claim 4, wherein said lubricant has a dynamic viscosity >20 cP at 40° C.

* * * * *